United States Patent [19]

Plattner et al.

[11] 4,161,488

[45] Jul. 17, 1979

[54] ENZYMATIC SUBSTRATES

[75] Inventors: Jacob J. Plattner; Houston F. Voss, both of Libertyville; Susan E. Magic, Lake Bluff, all of Ill.

[73] Assignee: Abbott Laboratories, North Chicago, Ill.

[21] Appl. No.: 934,297

[22] Filed: Aug. 17, 1978

[51] Int. Cl.² ............... C07C 153/11; C07C 101/00
[52] U.S. Cl. ................................. 260/455 R; 560/34
[58] Field of Search ................... 260/455 R; 560/34

[56] References Cited

U.S. PATENT DOCUMENTS

| | | | |
|---|---|---|---|
| 3,884,896 | 5/1975 | Blomback et al. | 260/112.5 R |
| 3,886,136 | 5/1975 | Claeson et al. | 260/112.5 R |
| 3,966,701 | 6/1976 | Dorman et al. | 260/112.5 R |

OTHER PUBLICATIONS

Klausner et al., Biochem. J. (1978), 169, pp. 157–167, Interaction of α-N-(p-toluenesulphonyl-)-p-quanidino-L-phenylalanine . . . .

Farmer et al., Use of N–Benzoyl–L–tyrosine Thiobenzyl Ester as a Protease Substrate, Journal of Biological Chemistry, vol. 250, No. 18, pp. 7366–7371 (1975).

*Primary Examiner*—John M. Ford
*Assistant Examiner*—Robert C. Whittenbaugh
*Attorney, Agent, or Firm*—John J. McDonnell; Robert L. Niblack

[57] ABSTRACT

The present invention encompasses the acid addition salts of a compound of the formula

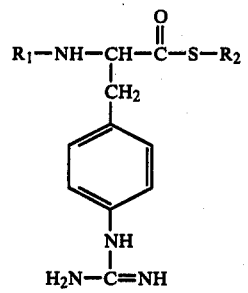

wherein $R_1$ represents phenylsulfonyl, benzoyl, carbobenzoxy, and the halo, loweralkyl having 1–4 carbon atoms, loweralkoxy having 1–3 carbon atoms, phenyl, or hydroxy substituted derivatives thereof; or alkanoyl having 2–12 carbon atoms; and $R_2$ represents alkyl having 1–10 carbon atoms, or alkoxyalkyl having 2–6 carbon atoms, cycloalkyl having 5–7 carbon atoms, or benzyl and the halo, loweralkyl having 1–4 carbon atoms, loweralkoxy having 1–3 carbon atoms, hydroxy, carboxy, or phenyl substituted derivatives thereof.

Compounds of the present invention are useful as analytical reagents. Enzymatic hydrolysis provides —S—$R_2$ which can be further reacted with 5,5′-dithiobis (2-nitrobenzoic acid) to provide a colored product by which the enzyme concentration can be determined spectrophotometrically.

9 Claims, No Drawings

ENZYMATIC SUBSTRATES

BACKGROUND OF THE INVENTION

The present invention relates to synthetic reagents or substrates which are used for the quantitative determination of proteolytic enzymes. More particularly, the invention relates to synthetic thioesters which are useful as a reagent for the quantitative determination of proteolytic enzyme of class E.C. 3.4.21, which split peptide chains on the carboxyl side of arginine as well as lysine in human and mammal body fluids as well as in vegetable and animal cell extracts and in glandular venoms of cold-blooded animals such as snakes.

Classical substrates for trypsin, thrombin and related enzymes have involved both esters such as α-N-tosyl-L-arginine methyl ester and α-N-tosyl-L-lysine methyl ester [G. W. Schwert et al., J. Biol. Chem., 172 (1948) 221; Sherry, S. and Troll, W., J. Biol. Chem., 208 (1954) 95; Elmore, D. T. and Curragh, Z. F. Biochem. J., 86 (1963)98]as well as amides such as α-N-benzoyl-DL-arginine-p-nitroanilide, L-lysine-p-nitroanilide, α-N-benzoyl-DL-arginine-2-naphthylamide and other di, tri and higher order arginine and lysine peptides with chromogenic amide leaving groups [B. F. Erlanger et al., Arch. Bioch. Biop. 96 (1961) 271; A. Redidel and E. Wunsch, Z. Physiol. Chem. 316 (1959) 1959; R. E. Plapinger et al., J. Org. Chem. 30 (1965) 1781; L. Svendsen et al., Thrombosis Res. 1 (1972) 267].

The use of ester substrates for this class of enzyme have been limited by the cumbersome assay procedures such as pH titration or detection of the small change in absorbance of the above products in the UV region of the spectra. The introduction of the amide chromogenic substrates based on p-nitroaniline or similar leaving groups have offered the advantage of an assay in the visible region of the spectra with by-products which have high extinction coefficients enabling more sensitive enzyme determinations to be made. The simple chromogenic substrate based only upon arginine or lysine amides have proved to be extremely poor substrates relative to the analogous esters [Erlanger et al., Arch. Bioch. Biop. 95 (1961) 271-8]. The advantage of extending the amino terminal end of either arginine or lysine p-nitroanilide substrates has been well documented and results in much improved substrate behavior, especially as determined by typical Michaelis-Menten kinetic parameters [Thrombosis Res 1 (1972) 267-78; U.S. Pat. No. 3,884,896, U.S. Pat. No. 4,061,625]. The difficulty in synthesizing these tri and tetra peptide materials has resulted in a high cost of the substrates and at the same time certain disadvantages such as limited solubility and inhibition of the enzymes by the cleaved product p-nitroaniline.

Farmer and Hageman, the Journal of Biological Chemistry, 250, 7366 (1975) describe the use of N-benzoyoyl-L-tyrosine thiobenzyl ester as a protease substrate detected by further reaction with 5,5'-dithiobis [2-nitrobenzoic acid].

Substrates of the present invention are particularly advantageous in that they have selective activities toward trypsin and they have excellent shelf life.

p-guanidino-L-phenylalanine methyl ester is known as a substrate for trypsin and as an inhibitor of thrombin, Klausner et al., Biochem. J. 169, 157-167 (1978). Compounds of the present invention provide reagents which are selective in their activity, have stable shelf life and the product of enzyme hydrolysis is readily converted to a colorimetric reagent.

BRIEF DESCRIPTION OF THE INVENTION

The present invention encompasses acid addition salts of the formula

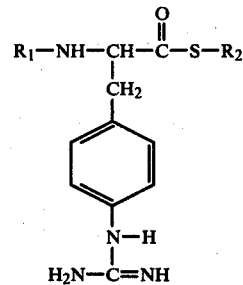

wherein $R_1$ represents phenylsulfonyl, benzoyl, carbobenzoxy, and the halo, loweralkyl having 1-4 carbon atoms, loweralkoxy having 1-3 carbon atoms, phenyl, or hydroxy substituted derivatives thereof; or alkanoyl having 2-12 carbon atoms and $R_2$ represents alkyl having 1-10 carbon atoms, or alkoxyalkyl having 2-6 carbon atoms, cycloalkyl having 5-7 carbon atoms, or benzyl and the halo, loweralkyl having 1-4 carbon atoms, loweralkoxy having 1-3 carbon atoms, carboxy, hydroxy, or phenyl substituted derivatives thereof.

Compounds of the present invention are useful as analytical reagents for detecting enzymes such as thrombin and trypsin. Enzymatic hydrolysis provides $-S-R_2$ which can be further reacted with 5,5'-dithiobis (2-nitrobenzoic acid) to produce a colored product by which the enzyme concentration can be indirectly determined spectrophotometrically.

DETAILED DESCRIPTION OF THE INVENTION

The present invention encompasses derivatives of

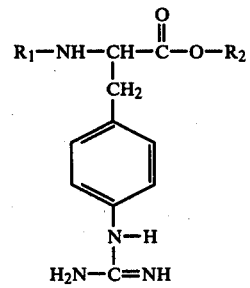

described in Klausner et al., Biochem. J. 169, 157-67 (1978). $R_1$ previously defined, represents common blocking groups for the amino moiety of an amino acid. Thus, $R_1$ is typically a radical of the formula

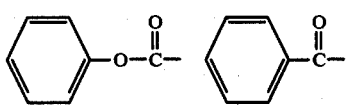

Carbobenzoxy,      Benzoyl,

-continued

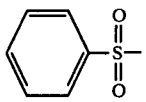 

Phenylsulfonyl, alkanoyl

The phenyl ring may be substituted with common substituents including: halo such as fluoro, chloro, bromo, and iodo; lower-alkyl such as methyl, ethyl, isopropyl, propyl, butyl, isobutyl, tertiery butyl, alkoxy such as methoxy, ethoxy, propoxy, hydroxy and phenyl. Those skilled in the chemical arts will recognize the equivalence of a large number of aromatic ring substituents.

The above indicated blocking groups are introduced by reacting methyl or ethyl ester the guanadino blocked by protonization with acids such as nitric or p-toluene sulfonic with an activated ester of the blocking group such as p-nitrophenyl-ester, pentachlorophenylester, N-hydroxysuccinimideester, acid azide, acid chloride, or acid anhydride. These techniques are well recognized in the peptide synthesis art, *J. chem. Soc.*, 3134 (1957), techniques for introducing blocking groups into the amino portion of an amino acid are described in (Archives of Biochemistry and Biophysics, 108, 266 (1964) and U.S. Pat. No. 3,884,896. Blocked acids and esters are converted to compounds of the present invention by exchanging esters with thiols corresponding to H—S—$R_2$ in acid or by converting blocked amino acids to the acid chloride by reaction with thionyl chloride followed by reaction with the H—S—$R_2$ thiol or by carbodiimide coupling of the mercaptan and blocked amino acid.

Typically, $R_2$ is a straight or branched chain lower-alkyl having 1–10 carbon atoms exemplified by methyl ethyl, propyl isopropyl, butyl, isobutyl, pentyl, hexyl, decyl and the like, cyclopentyl, cyclohexyl, cycloheptyl, ethoxyethyl, methoxypropyl are examples of other groups represented by $R_2$. $R_2$ also represents benzyl and benzyl substituted with halo such as fluoro, chloro, bromo, iodo, loweralkyl such as methyl, ethyl, propyl, isopropyl, butyl, isobutyl, tertiery butyl, alkoxy such as methoxy, ethoxy, hydroxy, carboxy, and phenyl. Phenyl substituted benzyl is meant to include biphenylmethyl and napthylmethyl.

In a typical preparation α-N-p-toluenesulfonyl-L-p-quanidinophenylalanine is reacted with an excess of thionyl chloride to provide the corresponding acid chloride. The acid chloride is in turn reacted with ethyl mercaptan to provide α-N-(p-toluenesulfonyl)-L-p-guanidinophenylalanine thioethylester hydrochloride which is purified by silica gel chromatography. Other acid addition salts are prepared by exchanging the above with acids such as sulfuric, hydrobromic, toluene sulfonic, phosphoric, acetic, carbonic, formic, benzoic, nitric, tetrafluorooboric, hydroiodic and the like on an ion exchange column. The acid addition salts are of the type which are biologically or pharmaceutically acceptable salts.

Preferred reagents in the scope of the present invention are

α-N-(p-toluenesulfonyl)-L-p-guanidinophenylalanine thioethylester

α-N-(p-toluenesulfonyl)-L-p-guanidinophenylalanine thiobenzylester

α-N-(p-toluenesulfonyl)-L-p-guanidinophenylalanine thioisopropylester

α-N-(p-toluenesulfonyl)-L-p-guanidinophenylalanine thioisobutylester

α-N-(p-toluenesulfonyl)-L-p-guanidinophenylalanine thiochlorobenzylester

α-N-(p-phenylsulfonyl)-L-p-guanidinophenylalanine thiodecylester

α-N-(p-methoxyphenylsulfonyl)-L-p-guanidinophenylalanine thiocyclohexylester

α-N-(p-chlorophenylsulfonyl)-L-p-guanidinophenylalanine thiophenylester

α-N-benzoyl-L-p-guanidinophenylalanine thiobenzylester

α-N-carbobenzoxy-L-p-guanidinophenylalanine thioethylester

α-N-carbobenzoxy-L-p-guanidinophenylalanine thiobenzylester

α-N-benzoyl-L-p-guanidinophenylalanine thioethylester

α-N-pivalyl-L-p-guanidinophenylalanine-p-ethoxybenzylthioester

α-N-p-chlorobenzoyl-L-p-guanidinophenylalanine-p-toluenethioester and the hydrochloride salts thereof.

Table 1 illustrates the usefulness of compounds of the present invention for determining thrombin and trypsin. Kinetic analysis of the compounds in Table 1 were carried out in pH 7.4, 0.1 potassium phosphate buffer with 0.1% gelatin to stabilize the enzymes used. Both purified trypsin and purified thrombin were utilized to obtain the indicated Michaelis-Menten kinetic constants. The analyses were performed with 0.16mM of 5,5'-dithiobis-(2-nitrobenzoic acid) in the reaction mixture and varying concentrations of enzymes as warranted by the turnover of the indicated substrate. The analyses were performed in a routine manner on an Abbott ABA-100 bichromatic analyzer with a 415-530 filter pair at 37° C. or with a Varian "Superscan" double beam spectrophotometer at 412nM. No difference in kinetic constants were seen when proper corrections were made to account for the bichromatic nature of the ABA-100 or the system. In all cases, the observed values of enzyme hydrolyses were corrected to account for spontaneous hydrolyses.

TABLE 1

| p-quanidinophenylalanine [α-N-tosyl] | Thrombin | | Trypsin | |
|---|---|---|---|---|
| | $K_{cat}$ $sec^{-1}$ | $K_m$ $\times 10^{5m}$ | $K_{cat}$ $sec^{-1}$ | $K_m$ $\times 10^{5m}$ |
| thioethylester | 1.53 | .96 | 1510 | 10 |
| thiobenzylester | 9.9 | 4.7 | 930 | 4.1 |

The compounds of the present invention are useful for measuring the amount of thrombin released from prothrombin in human plasma. In particular, the compound of the present invention are useful for measuring levels of antithrombin III in plasma samples. Thus, the reagent is added to plasma samples after inhibition by antithrombin III. The hydrolysis product —S—$R_2$ is trapped by 5,5'-dithiobis-(2-nitrobenzoic acid) to form a colored product detectable spectrophotometrically.

The following examples are set out to illustrate the present invention and are not to limit it in scope or spirit.

EXAMPLE I

To 231 mg of α-N-toluenesulfonyl-L-p-guanidinophenylalanine (Klausner et al., *Biochem. J.* 169 157

(1978) is added 2 ml of thionyl chloride and the resulting mixture stirred vigorously in a water bath at 15°–20° C. After 6–8 minutes a heavy oil separates and stirring is continued for an additional 8–10 minutes at −15° C. (ice methanol bath). The cooled mixture is treated with 25 ml of ethylether to form a gummy precipitate. The supernatant liquid is decanted and the residue triturated several times with ether. Upon scratching in chilled ether the gummy material is transformed into a pale yellow solid which is separated from the ether by inverse filtration. Two ml of ethyl mercaptan is added to the solid acid chloride and the mixture cooled to 15° C. 0.5 ml of dimethylformamide is added with vigorous stirring. After stirring for 30–45 minutes at room temperature ether is added causing a gum to separate. The gum is dissolved in methylene chloride and reprecipitated with ethyl ether. The product is chromatographed on silica gel eluting with 3–4% water in acetonitrile to provide α-N-(p-toluenesulfonyl)-L-p-guanidinophenylalanine thioethylester hydrochloride having the formula

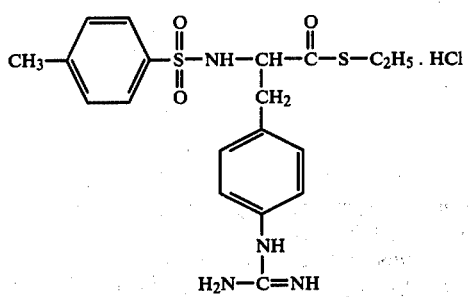

Freeze drying an aqueous solution of the thioester provides a white powder characterized as follows: Rf 0.37, 10% water in acetonitrile; NMR (methanol-Cl$_4$): 1.05 (3H, triplet, SCH$_2$CH$_3$), 2.38 (3H, singlet, Ar-CH$_3$); 2.85 (2H, quartet, SCH$_2$CH$_3$); 7.16–7.73 (8H, multiplet, aromatic).

EXAMPLE II

Following the procedure in Example 1 replacing ethylmercaptan with phenylmethylmercaptan provides α-N-(p-toluenesulfonyl)-L-p-guanidinophenylalanine thiobenzylester hydrochloride.

EXAMPLE III

Following the procedure in Example 1 replacing ethylmercaptan with isobutylmercaptan provides α-N-(p-toluenesulfonyl)-L-p-guanidinophenylalanine thioisobutylester.

EXAMPLE IV

Following the procedure in Example 1 replacing ethylmercaptan with isopropylmercaptan provides α-N-(p-toluenesulfonyl)-L-p-guanidinophenylalanine thioisopropylester hydrochloride.

EXAMPLE V

Following the procedure in Example 1 replacing ethylmercaptan with p-chlorophenylmethyl mercaptan provides α-N-(p-toluenesulfonyl)-L-p-guanidinophenylalanine thio-p-chlorobenzylester.

EXAMPLE VI

Following the procedure in Example 1 replacing α-N-toluenesulfonyl-L-p-guanidinophenylalanine with α-N-carbobenzoxy-L-p-guanidinophenylalanine, thioethylester hydrochloride of the formula

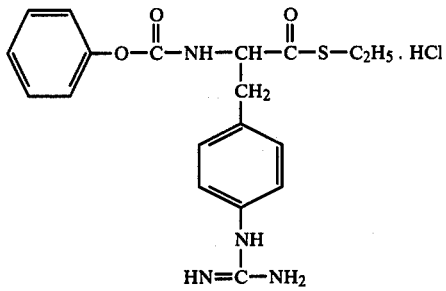

and the free base. Replacing ethylmercaptan with phenylmethylmercaptan provides α-N-carbobenzoxy-L-p-guanidinophenylalanine thiobenzylester hydrochloride and the free base.

EXAMPLE VII

Following the procedure in Example 1 using α-N-benzoyl-L-p-guanidinophenylalanine provides α-N-benzoyl-L-p-guanidinophenylalanine thioethylester hydrochloride having the formula

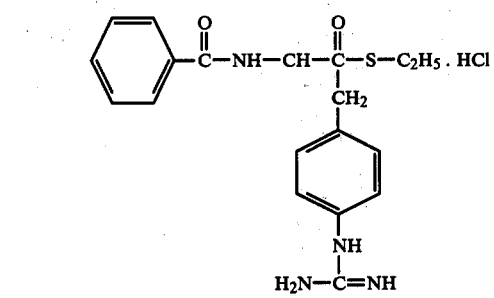

and the free base. Replacing ethylmercaptan with phenylmethylmercaptan provides α-N-benzoyl-L-p-guanidinophenylalanine thiobenzylester hydrochloride.

EXAMPLE VIII

α-N-acetyl p-guanidinophenylalanine prepared by reaction of acetic anhydride with the nitric acid salt of p-guanidinophenylalanine is used to replace α-N-toluenesulfonyl-L-p-guanidinophenylalanine in Example 1 to provide α-N-acetyl-L-p-guanidinophenylalanine thioethylester hydrochloride, having the formula

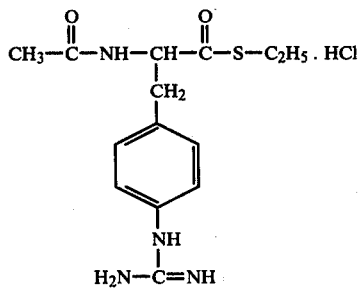

Replacing ethylmercaptan with phenylmethylmercaptan provides α-N-acetyl-L-p-guanidinophenylalanine thiobenzylester hydrochloride.

What is claimed is:

1. The biologically compatible acid addition salts of a compound of the formula

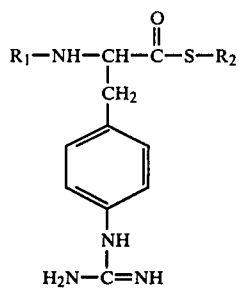

wherein $R_1$ represents phenylsulfonyl, benzoyl, carbobenzoxy, and the halo, loweralkyl having 1–4 carbon atoms, loweralkoxy having 1–3 carbon atoms, phenyl, or hydroxy substituted derivatives thereof, or alkanoyl having 2–12 carbon atoms; and $R_2$ represents alkyl having 1–10 carbon atoms, or alkoxyalkyl having 2–6 carbon atoms, cycloalkyl having 5–7 carbon atoms, or benzyl, and the halo, loweralkyl having 1–4 carbon atoms, loweralkoxy having 1–3 carbon atoms, carboxy, hydroxy, or phenyl substituted derivatives thereof.

2. The biologically compatible acid addition salts of a compound according to claim 1 of the formula

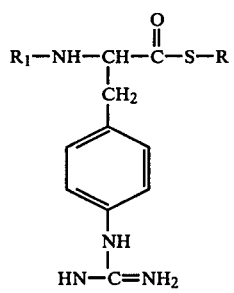

wherein R represents alkyl having 1–6 carbon atoms.

3. The biologically compatible acid addition salts of a compound according to claim 1 of the formula

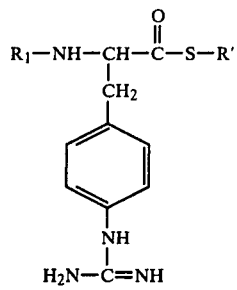

wherein R' represents benzyl or halobenzyl.

4. The biologically compatible acid addition salts of a compound of the formula

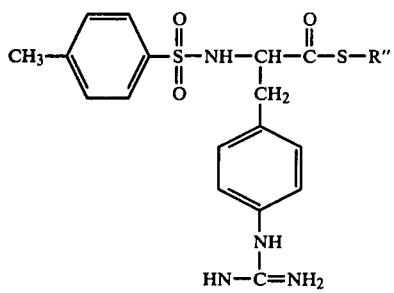

wherein R" represents alkyl having 1–6 carbon atoms, benzyl, or halobenzyl.

5. A compound according to claim 4 which is α-N-toluenesulfonyl-p-guanidinophenylalanine thioethylester hydrochloride.

6. A compound according to claim 4 which is α-N-toluenesulfonyl-p-guanidinophenylalanine thioisopropylester hydrochloride.

7. A compound according to claim 4 which is α-N-toluenesulfonyl-p-guanidinophenylalanine thioisobutylester hydrochloride.

8. A compound according to claim 3 which is α-N-toluenesulfonyl-p-guanidinophenylalanine thiobenzylester hydrochloride.

9. A compound according to claim 3 which is toluenesulfonyl-p-guanidinophenylalanine thio(p-chlorobenzyl) ester hydrochloride.

* * * * *